(12) United States Patent
Nishii et al.

(10) Patent No.: US 7,881,433 B2
(45) Date of Patent: Feb. 1, 2011

(54) DISPLAY CONTROL APPARATUS, RADIATION IMAGING APPARATUS, AND RADIATION IMAGING SYSTEM

(75) Inventors: Yuichi Nishii, Tokyo (JP); Koji Takekoshi, Yokohama (JP); Hideto Shiozawa, Suwa (JP)

(73) Assignee: Canon Kabushiki Kaisha, Tokyo (JP)

( * ) Notice: Subject to any disclaimer, the term of this patent is extended or adjusted under 35 U.S.C. 154(b) by 71 days.

(21) Appl. No.: 12/255,337

(22) Filed: Oct. 21, 2008

(65) Prior Publication Data
US 2009/0103676 A1 Apr. 23, 2009

(30) Foreign Application Priority Data
Oct. 23, 2007 (JP) .............................. 2007-275648

(51) Int. Cl.
*H05G 1/64* (2006.01)
*H05G 1/58* (2006.01)
(52) U.S. Cl. ......................................... 378/98; 378/116
(58) Field of Classification Search .................... 378/4, 378/19, 91, 98, 98.5, 98.8, 114–116, 162, 378/165, 204, 210; 382/128, 130–132, 164, 382/173, 174, 190, 191, 302, 303, 305, 306, 382/325; 600/407, 408, 425
See application file for complete search history.

(56) References Cited

U.S. PATENT DOCUMENTS

| 5,090,042 | A * | 2/1992 | Bejjani et al. ............... 378/98.2 |
| 6,400,789 | B1 * | 6/2002 | Dafni ........................... 378/15 |
| 7,344,305 | B2 * | 3/2008 | Kuzmanovic ................ 378/206 |
| 2003/0223540 | A1 * | 12/2003 | Hayashida et al. ......... 378/98.8 |
| 2005/0220270 | A1 * | 10/2005 | Kameshima et al. ........ 378/116 |
| 2006/0291612 | A1 * | 12/2006 | Nishide et al. .................. 378/4 |
| 2008/0279334 | A1 * | 11/2008 | Takenaka et al. ............ 378/116 |

FOREIGN PATENT DOCUMENTS

JP 2000-012280 A 1/2000

* cited by examiner

*Primary Examiner*—Edward J Glick
*Assistant Examiner*—Anastasia Midkiff
(74) *Attorney, Agent, or Firm*—Canon U.S.A., Inc. I.P. Division

(57) ABSTRACT

In a display control apparatus, an image receiving portion receives a plurality of images sequentially transmitted from an X-ray imaging apparatus based on a transmission order determined by a transmission-order determining portion, and a capture-order information receiving portion also receives, from the X-ray imaging apparatus, capture-order information indicating a capture order in which each of the images was captured by the X-ray imaging apparatus. The images received by the image receiving portion are stored in an image storage memory. A display controller controls displaying of the images stored in the image storage memory on a display apparatus based on a transmission order for transmitting the images or the capture-order information in accordance with an input imaging condition and an operating status of the X-ray imaging apparatus.

8 Claims, 11 Drawing Sheets

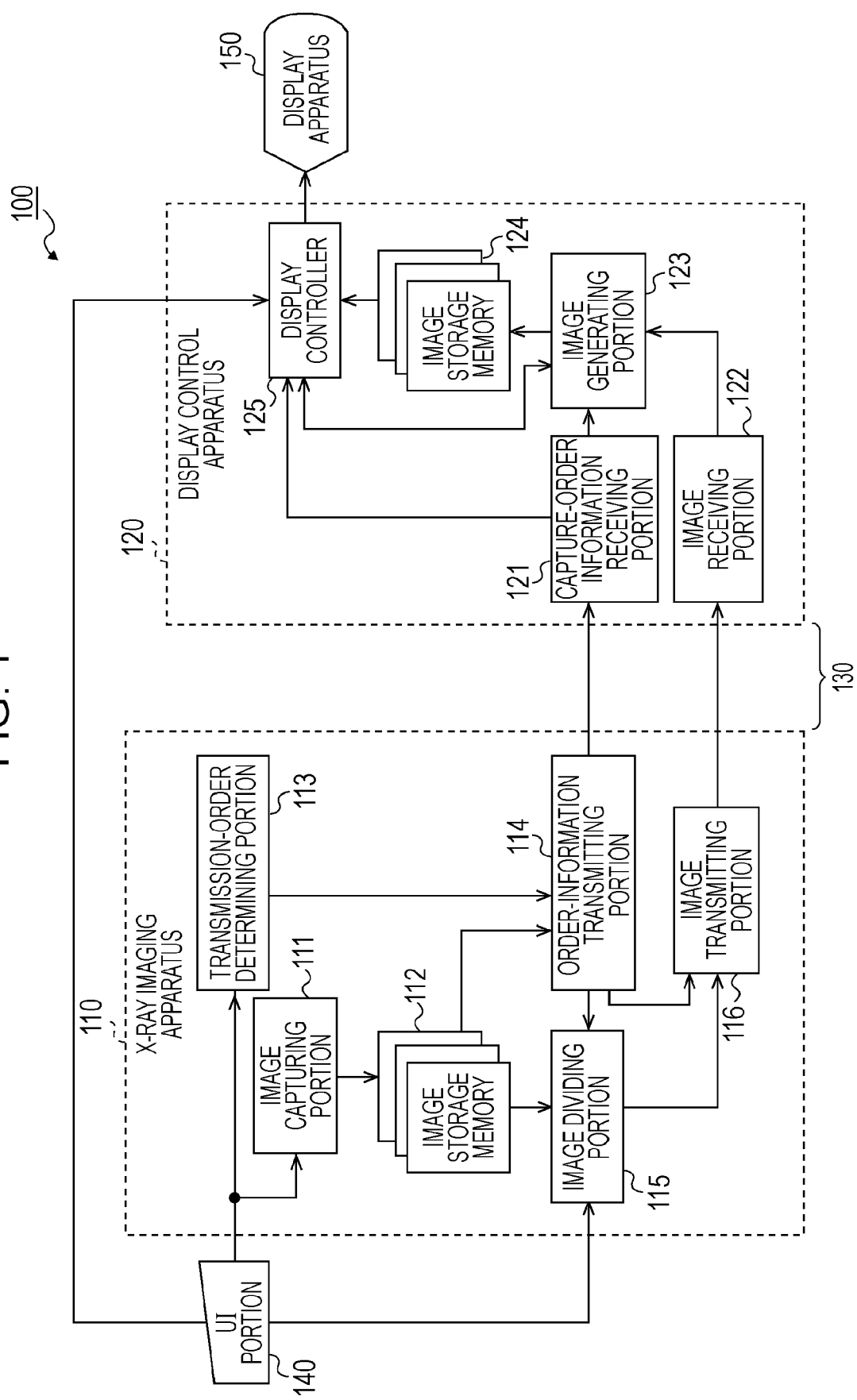

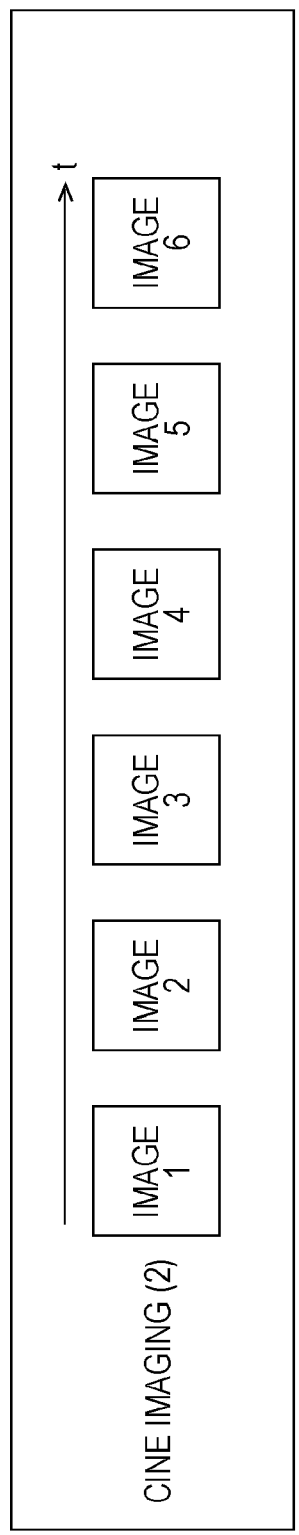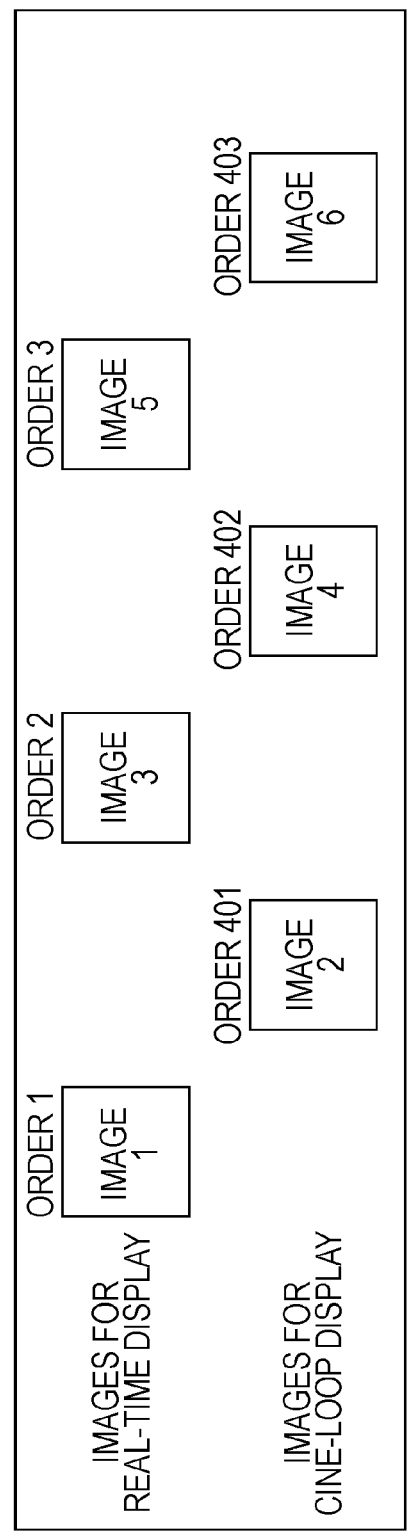
FIG. 5A
FIG. 5B

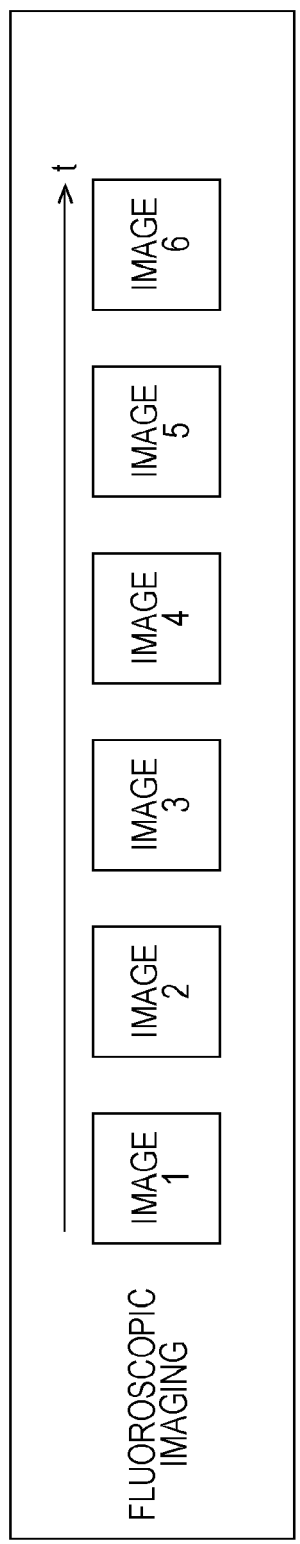
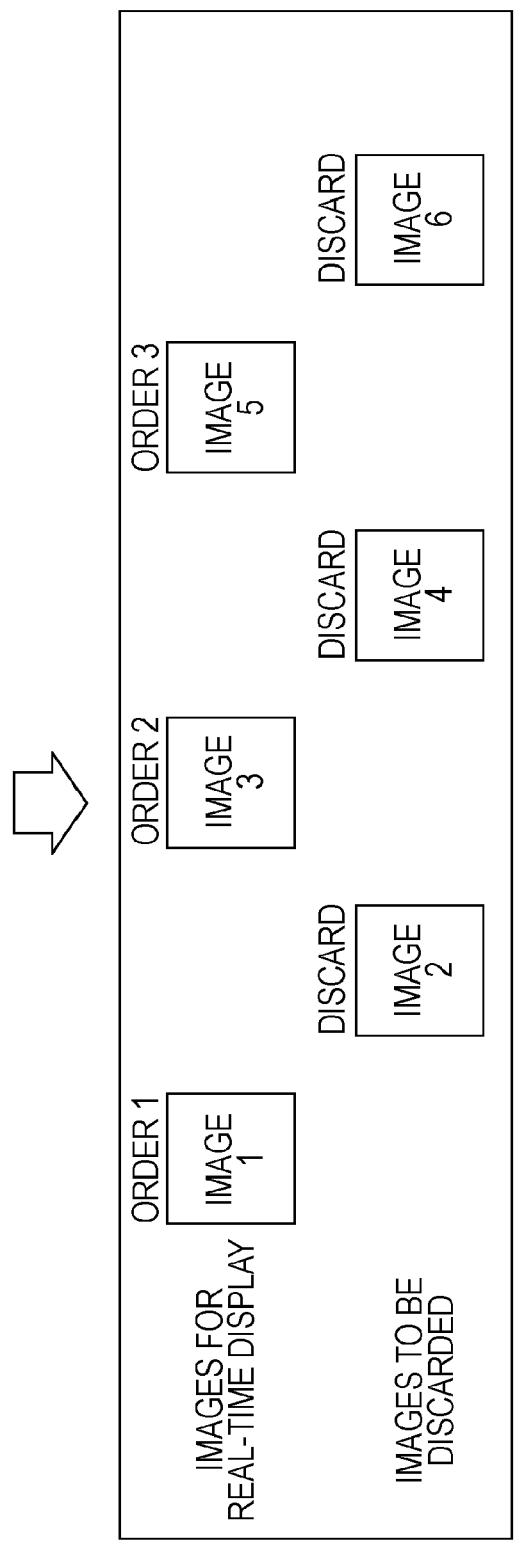
FIG. 6A
FIG. 6B

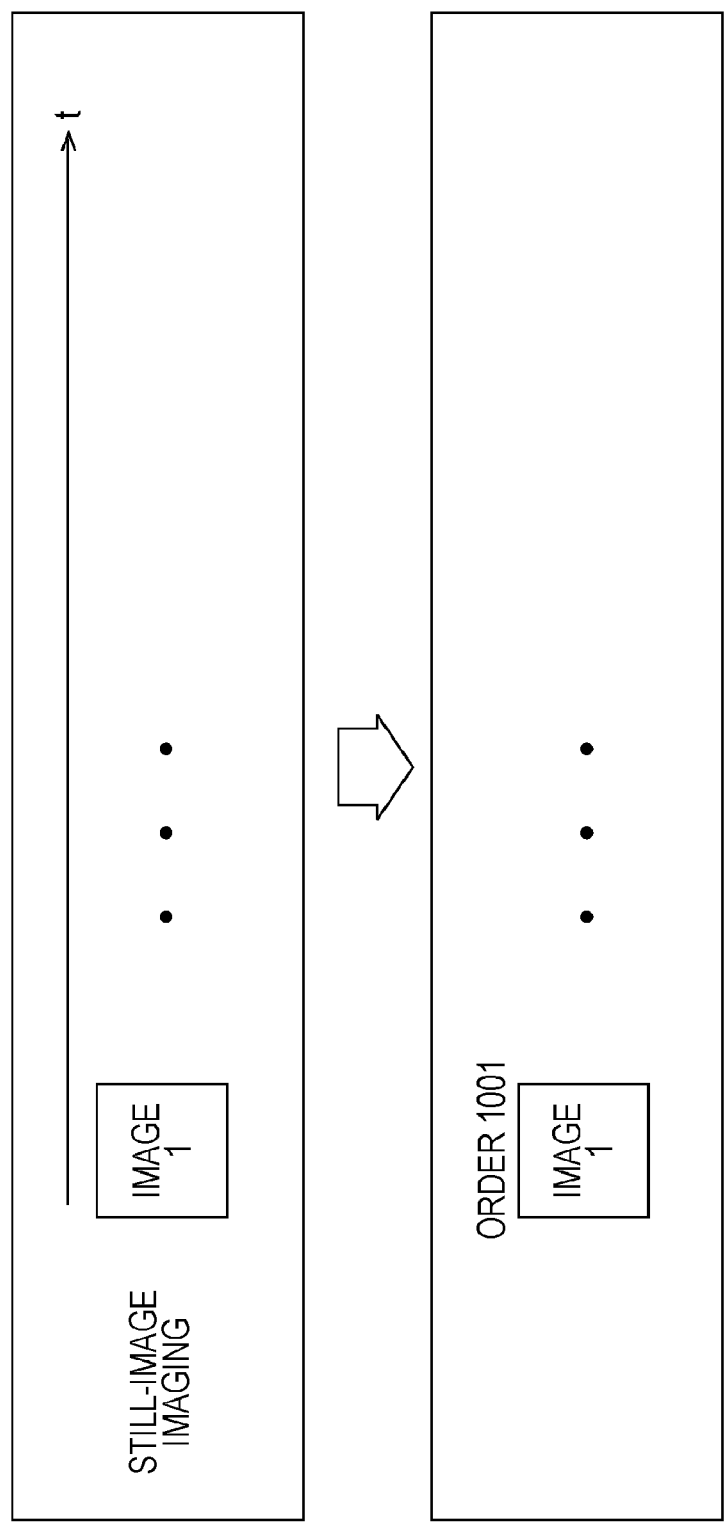

DISPLAY CONTROL APPARATUS, RADIATION IMAGING APPARATUS, AND RADIATION IMAGING SYSTEM

BACKGROUND OF THE INVENTION

1. Field of the Invention

The present invention relates to a radiation imaging apparatus for capturing an image, a driving method therefor, a display control apparatus for displaying an image captured by a radiation imaging apparatus, a display controlling method, and a radiation imaging system that includes a radiation imaging apparatus and a display control apparatus.

2. Description of the Related Art

An X-ray imaging system that performs fluoroscopy in real time for interventional radiology (IVR) or other purposes typically includes an X-ray imaging apparatus, a display control apparatus, and a display apparatus. Traditionally, an image intensifier and an analog pickup tube or charge-coupled device (CCD) coupled to the image intensifier are used in such an X-ray imaging apparatus. The X-ray imaging apparatus transmits analog data to a display control apparatus through a video signal, and the display control apparatus displays an image captured in analog form on a display apparatus, such as a cathode ray tube (CRT) monitor. One example of such an X-ray imaging apparatus employing an image intensifier is described in Japanese Patent Laid-Open No. 2000-012280.

As recent digitization proceeds, an image intensifier (and analog pickup tube or CCD) in an X-ray imaging apparatus is being replaced by a flat panel sensor (FPS). With this trend, a CRT monitor or other monitors is being replaced by a high-definition liquid-crystal monitor using the digital visual interface (DVI), so a full digital system in which the process from imaging to displaying is digitized is being established.

However, for the above-described full-digital X-ray imaging system, if the speed of capturing an image is high or the resolution of image data is high in the X-ray imaging apparatus, a band for use in a communication unit that connects the X-ray imaging apparatus and the display control apparatus may be insufficient. This may cause a lag in transmission of image data from the X-ray imaging apparatus to the display control apparatus, and may result in a delay in displaying on the display apparatus.

By contrast, if image data is subjected to lossy compression or sampled in order not to cause a display delay, the image data will lose quality and thus the image displayed on the display apparatus will be degraded. This may lead to troubles in medical treatment, for example.

In particular, in an X-ray imaging system performing cine imaging, "cine-loop displaying" in which all images are displayed in a loop after the completion of the imaging and "real time displaying" in which display delay is less during the imaging are carried out. Therefore, it is necessary to satisfy both the conditions for cine-loop displaying and the conditions for real time displaying.

SUMMARY OF THE INVENTION

The present invention has been made in consideration of the above situation. The present invention provides a technique for suppressing a delay in displaying an image without degrading the image.

According to an aspect of the present invention, a display control apparatus for controlling displaying of a plurality of images captured by a radiation imaging apparatus on a display apparatus is provided. The display control apparatus includes an image receiving unit, a capture-order information receiving unit, a storage unit, and a display control unit. The image receiving unit is configured to receive a plurality of images sequentially transmitted from the radiation imaging apparatus in accordance with a determined transmission order. The capture-order information receiving unit is configured to receive, from the radiation imaging apparatus, capture-order information associated with each of the plurality of images and indicating a capture order in which the images were captured by the radiation imaging apparatus. The storage unit is configured to store the images received by the image receiving unit. The display control unit is configured to control displaying of the images stored in the storage unit on the display apparatus based on the transmission order or the capture-order information in accordance with an input imaging condition and an operating status of the radiation imaging apparatus.

Further features of the present invention will become apparent from the following description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is a block diagram of an X-ray imaging system (radiation imaging system) according to an embodiment of the present invention.

FIGS. 5A and 5B are schematic diagrams that illustrate one example transmission order determined by the transmission-order determining portion when a second cine imaging is performed.

FIGS. 6A and 6B are schematic diagrams that illustrate one example transmission order determined by the transmission-order determining portion when a fluoroscopic imaging is performed.

FIGS. 7A and 7B are schematic diagrams that illustrate one example transmission order determined by the transmission-order determining portion when a still-image imaging is performed.

DESCRIPTION OF THE EMBODIMENTS

Figure 2A:
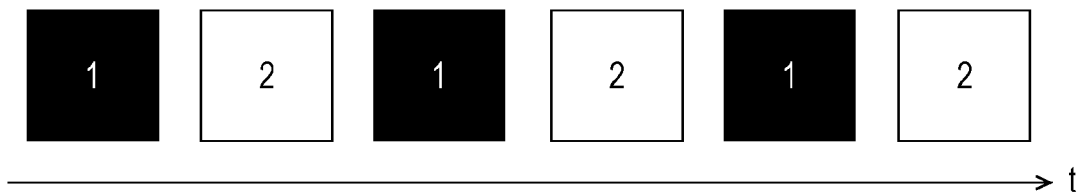
FIGS. 2A to 2E are schematic diagrams that illustrate examples of the process performed in an image dividing portion of an X-ray imaging system (radiation imaging system) according to an embodiment of the present invention.

Embodiments of the present invention are described in detail below in accordance with the accompanying drawings.

Best mode for carrying out the invention is described below with reference to the accompanying drawings. In the description below for a radiation imaging apparatus according to embodiments of the present invention, an X-ray imaging apparatus is used, which employs an X ray as radiation, by way of example. However, the radiation used in the present invention is not limited to an X ray. Examples of the radiation usable in the present invention include an α ray, β ray, and γ ray. An apparatus that processes a radiologic image captured using any one of the aforementioned ray is also included in the present invention.

In FIG. 1, an X-ray imaging apparatus 110 is connected to a display control apparatus 120 controlling displaying performed in a display apparatus 150 so as to be able to communicate with the display control apparatus 120. The X-ray imaging apparatus 110 irradiates a subject with X rays to capture an X-ray image based on X rays passing through the subject. The display control apparatus 120 controls displaying a plurality of images captured by the X-ray imaging apparatus 110 on the display apparatus 150. A communication unit 130 connects the X-ray imaging apparatus 110 and the display control apparatus 120 such that both apparatuses can communicate with each other. The communication unit 130 can use Ethernet® or camera link, for example. A user interface (UI) portion 140 is operated by a user when the user provides an X-ray imaging system 100 with an input instruction. The display apparatus 150 displays, for example, an image captured by the X-ray imaging apparatus 110 under the control of displaying performed by the display control apparatus 120.

An internal configuration of the X-ray imaging apparatus 110 will now be described below.

As illustrated in FIG. 1, the X-ray imaging apparatus 110 includes an image capturing portion 111, an image storage memory 112, a transmission-order determining portion 113, an order-information transmitting portion 114, an image dividing portion 115, and an image transmitting portion 116.

The image capturing portion 111 captures a plurality of images of a subject.

For example, the image capturing portion 111 can include an X-ray generator (radiation generator) for emitting an X-ray from an X-ray tube to a subject and a converter for converting an X ray passing through the subject (an X-ray image) into visible radiation (visible radiation image) to generate image data based on the visible radiation image. As the converter, the aforementioned image intensifier or a planar detector in which pixels including detecting elements and switching elements are two-dimensionally arranged can be used, for example.

In the case where the image intensifier is used as the converter, an X-ray image generated by X rays passing through a subject is converted into electrons and multiplied, and the converted image is then converted into a visible radiation image at the output surface to acquire image data.

In the case where the planar detector is used as the converter, X rays incident on the two-dimensionally arranged detecting elements are detected as charges proportional to an X-ray dose (hereinafter referred to as "signal carries"). Then, the signal carriers detected by the detecting elements are read by the switching elements, for example, thin-film transistors (TFTs). After the read signal carriers are converted into a voltage, analog-to-digital conversion is performed thereon. In such a way, image data composed of a digital signal is acquired.

The image storage memory 112 temporarily stores a plurality of images (image data) captured by the image capturing portion 111.

The transmission-order determining portion 113 first determines the priority of each of images obtained by the image capturing portion 111 in accordance with an imaging condition input from the UI portion 140. The transmission-order determining portion 113 then determines a transmission order for transmitting the images captured by the image capturing portion 111 to the display control apparatus 120 in accordance with the determined priorities and the time when each of the images was captured. The transmission-order determining portion 113 then transmits transmission-order information indicating the determined transmission order to the order-information transmitting portion 114.

The order-information transmitting portion 114 transmits, to the display control apparatus 120, capture-order information that is associated with each of the images stored in the image storage memory 112 and that indicates a capture order in which the image was captured. The order-information transmitting portion 114 also transmits the transmission-order information, transmitted from the transmission-order determining portion 113, to the image dividing portion 115 and the image transmitting portion 116. Here, the capture-order information is determined in accordance with the time when the image was captured by the image capturing portion 111.

The image dividing portion 115 divides images stored in the image storage memory 112 as needed in accordance with input information input from the UI portion 140. At this time, the image dividing portion 115 acquires the images from the image storage memory 112 using, for example, pointer reference in accordance with the transmission-order information determined by the transmission-order determining portion 113 and divides the images.

The image transmitting portion 116 sequentially transmits a plurality of images stored in the image storage memory 112 to the display control apparatus 120 in accordance with the transmission order determined by the transmission-order determining portion 113, i.e., the transmission-order information transmitted from the order-information transmitting portion 114. Here, if images stored in the image storage memory 112 are divided by the image dividing portion 115, the image transmitting portion 116 transmits the images divided by the image dividing portion 115 to the display control apparatus 120 in accordance with transmission-order information transmitted from the order-information transmitting portion 114.

The X-ray imaging apparatus 110 may alternatively include a plurality of image transmitting portions 116, and any of the image transmitting portions may transmit an image to the display control apparatus 120 in accordance with a transmission order determined by the transmission-order determining portion 113. Moreover, the order-information transmitting portion 114 and the image transmitting portion(s) 116 may alternatively be connected to the display control apparatus 120 with the same communication unit 130 or different communication units 130 therebetween.

An example method of driving the X-ray imaging apparatus 110 having the configuration described above will now be described below.

First, in accordance with an imaging condition input through the UI portion 140, the image capturing portion 111 captures a plurality of images for a subject and generates the captured images (image data). The plurality of images (image data) generated by the image capturing portion 111 is temporarily stored in the image storage memory 112.

At the same time, the transmission-order determining portion 113 determines a transmission order for transmitting the images to the display control apparatus 120 using the imaging condition input through the UI portion 140 and time information indicating the time when each of the images was captured. Transmission-order information indicating the transmission order determined by the transmission-order determining portion 113 is transmitted to the image dividing portion 115 via the order-information transmitting portion 114.

The image dividing portion 115 acquires images from the image storage memory 112 in accordance with the transmission-order information and divides the images as needed. The image transmitting portion 116 transmits the images acquired by the image dividing portion 115 or the images acquired by the image dividing portion 115 and then divided thereby to the display control apparatus 120 in accordance with the transmission-order information transmitted from the order-information transmitting portion 114.

Examples of the imaging condition input through the UI portion 140 include an imaging mode, including cine imaging, fluoroscopic imaging, still-image imaging, snap-shot imaging, and digital subtraction angiography (DSA) imaging. The imaging condition is not limited to such an imaging mode. Any one of a part of a subject to be radiographed, a condition of X-rays with which a subject is irradiated, a frame rate for radiographing, a size of an image to be captured, a bit depth, color information, and a dynamic range of the image can also be used.

FIGS. 2A to 2E are schematic diagrams that illustrate examples of the process performed in the image dividing portion 115 of the X-ray imaging apparatus (radiation imaging apparatus) according to an embodiment of the present invention.

One example is illustrated in FIG. 2A. In this example, images are divided by use of a process of dividing a plurality of images stored in the image storage memory 112 chronologically (on an image-by-image basis). An image indicated by "1," "2," or other figures in FIG. 2A can be an image of, for example, one frame. According to the process illustrated in FIG. 2A, each one of the images stored in the image storage memory 112 is not divided.

Figure 2B:
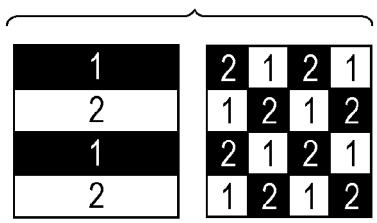
Figure 2C:
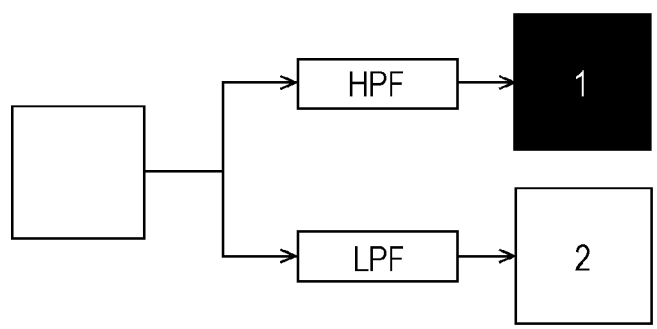
Figure 2D:
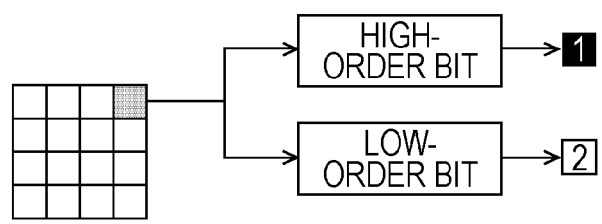
Figure 2E:
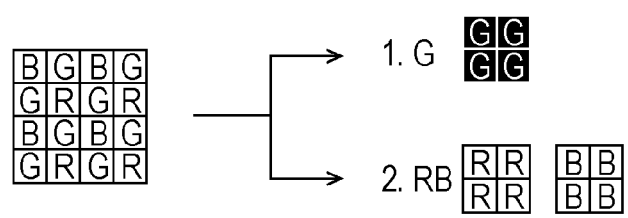

The image dividing portion 115 can divide each of the images stored in the image storage memory 112 by use of any one of the diving processes illustrate FIGS. 2B to 2E. More specifically, FIG. 2B illustrates a process of dividing an image in two on a pixel basis; FIG. 2C illustrates a process of dividing an image in two on a frequency basis; FIG. 2D illustrates a process of dividing an image in two on a bit-depth basis; and FIG. 2E illustrates a process of dividing an image in two on a color-information basis.

That is, each of images sequentially transmitted from the image transmitting portion 116 is an image of one frame captured by the image capturing portion 111 or divided image sections in which the one-frame image is divided.

An example process of determining a transmission order performed by the transmission-order determining portion 113 will now be described below.

Figure 3:
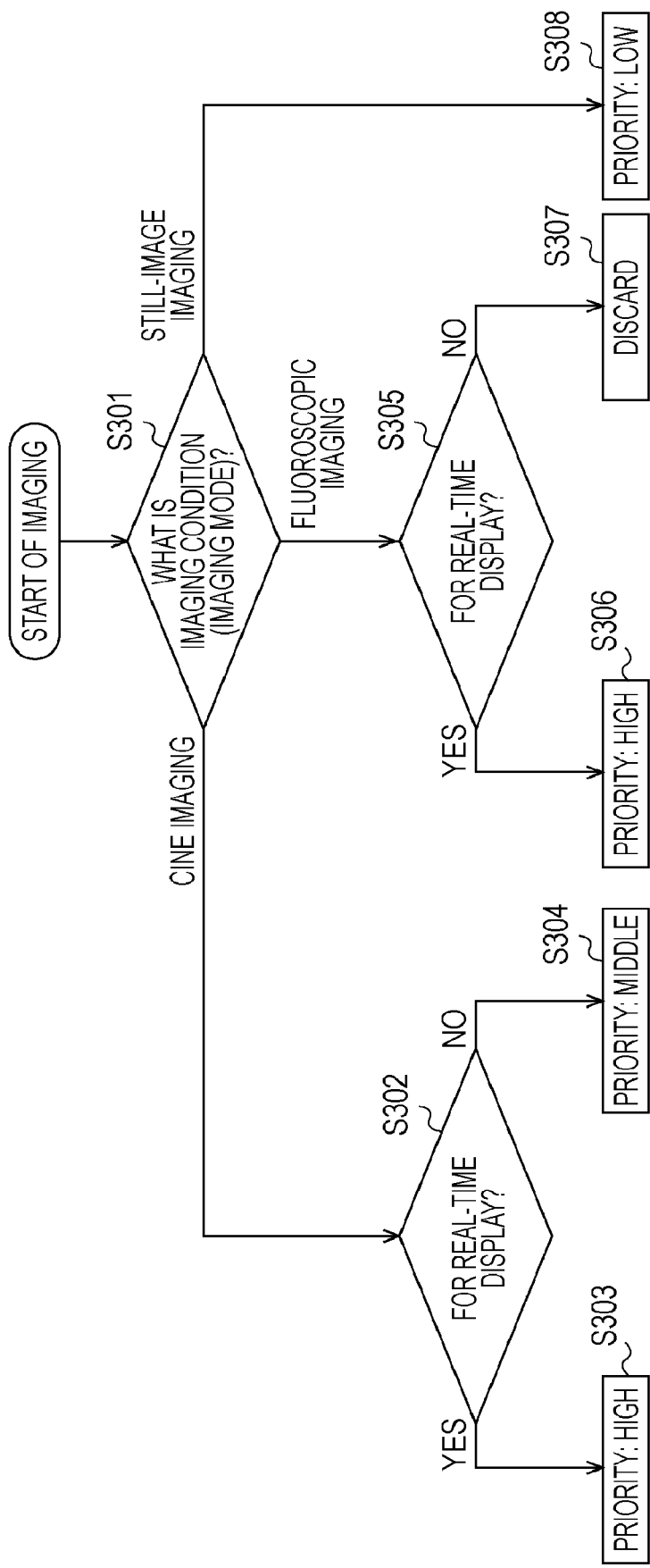
FIG. 3 is a flowchart that shows one example process of determining a transmission order performed by a transmission-order determining portion of an X-ray imaging system (radiation imaging system) according to an embodiment of the present invention.

FIG. 3 is a flowchart that shows one example of a process of determining a transmission order performed by the transmission-order determining portion 113 of the X-ray imaging apparatus (radiation imaging apparatus) according to an embodiment of the present invention.

In the example illustrated in FIG. 3, as an imaging condition input through the UI portion 140, an imaging mode consisting of "cine imaging," "fluoroscopic imaging," and "still-image imaging" is used. In this example, as the process performed by the image dividing portion 115, the chronologically dividing process illustrated in FIG. 2A (i.e., the process in which each one of images stored in the image storage memory 112 is not divided) is used.

When an imaging starts in response to an operation to the UI portion 140, in step S301, the transmission-order determining portion 113 determines what an imaging condition (in this embodiment, "imaging mode") input through the UI portion 140 is. If it is determined that the imaging mode is a cine imaging in step S301, flow proceeds to step S302. In step S302, the transmission-order determining portion 113 determines whether images captured by the image capturing portion 111 are images to be displayed in real time (hereinafter referred to as "images for real-time display"), using band information (frequency band information) of the communication unit 130, which connects the X-ray imaging apparatus 110 and the display control apparatus 120.

If it is determined that the images are images for real-time display in step S302, flow proceeds to step S303. In step S303, the transmission-order determining portion 113 determines that the priority is "high" with the aim of displaying the images with short display delay and determines a transmission order for the images for real-time display in accordance with the determined priority ("high") and the time when each of the images was captured. This associates transmission-order information indicating the transmission order with the images for real-time display.

If it is determined that the images are not images for real-time display in step S302, i.e., that the images are to be images to be displayed in a cine loop, flow proceeds to step S304. In step S304, the transmission-order determining portion 113 determines that their priority is "middle" as the priority after the images for real-time display and determines a transmission order for the images to be displayed in a cine loop (hereinafter referred to as "images for cine-loop display") in accordance with the determined priority ("middle") and the time when each of the images was captured. This associates transmission-order information indicating the transmission order with the images for cine-loop display.

Figure 4A:
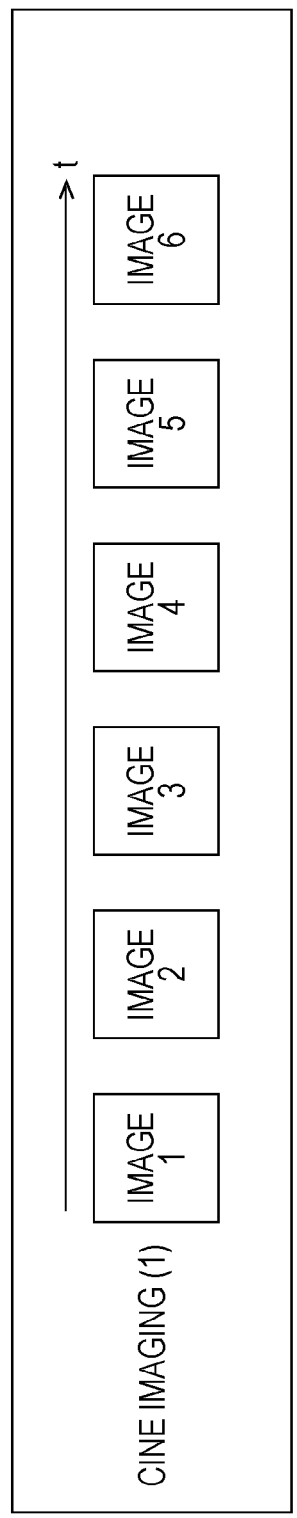
FIGS. 4A and 4B are schematic diagrams that illustrate one example transmission order determined by the transmission-order determining portion when a first cine imaging is performed.
Figure 4B:
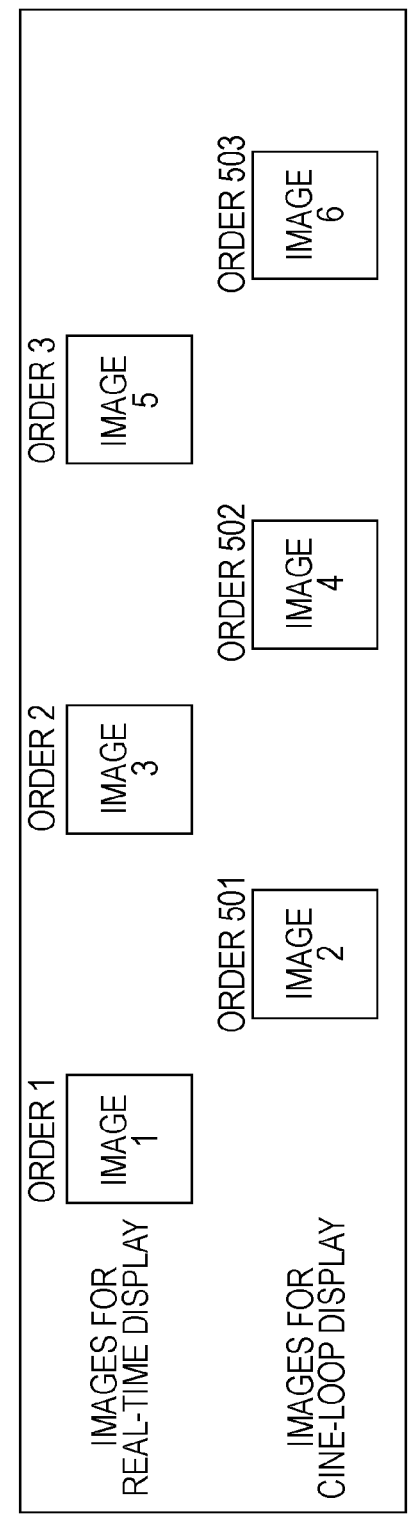

FIGS. 4A and 4B are schematic diagrams that illustrate one example transmission order determined by the transmission-order determining portion 113 when a cine imaging is performed. FIG. 4A illustrates images captured by the image capturing portion 111 in the cine imaging. The number assigned to each of images illustrated in FIG. 4A is capture-order information indicating a capture order in which the image was captured by the image capturing portion 111, for example.

For example, when images 1, 3, and 5 among the images illustrated in FIG. 4A are images for real-time display, the transmission-order determining portion 113 can assign an order 1 to the image 1, assign an order 2 to the image 3, and assign an order 3 to the image 5, for example. When images 2, 4, and 6 among the images illustrated in FIG. 4A are images for cine-loop display, the transmission-order determining portion 113 can assign an order 501 to the image 2, assign an order 502 to the image 4, and assign an order 503 to the image 6, for example. Here, images having high priorities are assigned lower order numbers as transmission-order information. In this case, images to which lower order numbers are assigned as transmission-order information are sequentially transmitted from the image transmitting portion 116 to the display control apparatus 120.

Alternatively, when the next cine imaging starts before the images for cine-loop display illustrated in FIG. 4B are transmitted, images for real-time display captured in the next cine imaging are first transmitted to the display control apparatus 120, as illustrated in FIGS. 5A and 5B. In this case, in order to perform cine-loop displaying, the images for cine-loop display captured in the next cine imaging illustrated in FIG. 5B are subsequently transmitted to the display control apparatus 120. This is because images to be first displayed in a cine loop are the images for real-time display captured in the next cine imaging. Therefore, the images for cine-loop display captured in the next cine imaging illustrated in FIG. 5B are assigned orders 401 to 403, which are lower than the orders to which the previous images for cine-loop display illustrated in FIG. 4B, for example. After that, the previous images for cine-loop display illustrated in FIG. 4B are transmitted to the display control apparatus 120.

Referring back to FIG. 3, if it is determined that the imaging mode is a fluoroscopic imaging in step S301, flow proceeds to step S305. In step S305, the transmission-order determining portion 113 determines whether images captured by the image capturing portion 111 are images for real-time display, using band information (frequency band information) of the communication unit 130, as in the case of the cine imaging.

If it is determined that the images are images for real-time display in step S305, flow proceeds to step S306. In step S306, the transmission-order determining portion 113 determines that the priority is "high" with the aim of displaying the images with a short display delay and determines a transmission order for the images for real-time display in accordance with the determined priority ("high") and the time when each of the images was captured. This associates transmission-order information indicating the transmission order with the images for real-time display, as in the case of the cine imaging.

If it is determined that the images are not images for real-time display in step S305, flow proceeds to step S307. In step S307, the transmission-order determining portion 113 does not assign transmission-order information to these images because cine-loop displaying is not necessary for a fluoroscopic imaging. As a result, these images are discarded without being transmitted to the display control apparatus 120.

FIGS. 6A and 6B are schematic diagrams that illustrate one example transmission order determined by the transmission-order determining portion 113 when a fluoroscopic imaging is performed. FIG. 6A illustrates images captured by the image capturing portion 111 in the fluoroscopic imaging. The number assigned to each of images illustrated in FIG. 6A is capture-order information indicating a capture order in which the image was captured by the image capturing portion 111, for example.

For example, when images 1, 3, and 5 among the images illustrated in FIG. 6A are images for real-time display, the transmission-order determining portion 113 can assign an order 1 to the image 1, assign an order 2 to the image 3, and assign an order 3 to the image 5, for example. When images 2, 4, and 6 among the images illustrated in FIG. 6A are images to be discarded, the transmission-order determining portion 113 does not assign transmission-order information to these images.

Referring back to FIG. 3, if it is determined that the imaging mode is a still-image imaging in step S301, flow proceeds to step S308. In step S308, the transmission-order determining portion 113 determines that the priority of the captured images is "low," which is lower than the priorities in the other modes, because the still-image imaging does not require very high real time performance, unlike in the other modes. The transmission-order determining portion 113 determines a transmission order for these still images in accordance with the determined priority ("low") and the time when each of the images was captured. This associates transmission-order information indicating the transmission order with the still images.

FIGS. 7A and 7B are schematic diagrams that illustrate one example transmission order determined by the transmission-order determining portion 113 when a still-image imaging is performed. FIG. 7A illustrates an image captured by the image capturing portion 111 in the still-image imaging. The number assigned to the image illustrated in FIG. 7A is capture-order information indicating a capture order in which the image was captured by the image capturing portion 111, for example.

For example, the image 1 illustrated in FIG. 7A can be assigned an order 1001, which is a priority lower than that in the other modes (cine imaging and fluoroscopic imaging), as transmission-order information, as illustrated in FIG. 7B.

Through steps S301 to S308 described above, a transmission order in which images are to be transmitted is determined by the transmission-order determining portion 113.

An internal configuration of the display control apparatus 120 illustrated in FIG. 1 will now be described below.

As illustrated in FIG. 1, the display control apparatus 120 includes a capture-order information receiving portion 121, an image receiving portion 122, an image generating portion 123, an image storage memory (storage unit) 124, and a display controller 125. The display control apparatus 120 acts as like a graphic board used to display an image transmitted from the X-ray imaging apparatus 110 on the display apparatus 150.

The capture-order information receiving portion 121 receives, from the order-information transmitting portion 114 of the X-ray imaging apparatus 110, capture-order information that is associated with each of images transmitted from the X-ray imaging apparatus 110 and that indicates a capture order in which the image was captured by the image capturing portion 111 of the X-ray imaging apparatus 110.

The image receiving portion 122 sequentially receives a plurality of images that have been sequentially transmitted from the image transmitting portion 116 of the X-ray imaging apparatus 110 in accordance with a transmission order determined by the transmission-order determining portion 113.

The image generating portion 123 generates a one-frame image using the capture-order information received by the capture-order information receiving portion 121 in the case where the image transmitting portion 116 sequentially transmits divided image sections acquired by division performed by the image dividing portion 115. At this time, the image generating portion 123 generates an image in response to a dividing process performed by the image dividing portion 115 under the control of the display controller 125 based on information input through the UI portion 140.

Specifically, for example, when the image dividing portion 115 divides an image using the dividing process illustrated in FIG. 2B, the image generating portion 123 generates a one-frame image using the capture-order information by a process of combining divided image sections on a pixel basis. Alternatively, for example, when the image dividing portion 115 divides an image using the dividing process illustrated in FIG. 2C, the image generating portion 123 generates a one-frame image using the capture-order information by a process of combining divided image sections on a frequency basis. Alternatively, for example, when the image dividing portion 115 divides an image using the dividing process illustrated in FIG. 2D, the image generating portion 123 generates a one-frame image using the capture-order information by a process of combining divided image sections on a bit-depth basis. Alternatively, for example, when the image dividing portion 115 divides an image using the dividing process illustrated in FIG. 2E, the image generating portion 123 generates a one-frame image using the capture-order information by a process of combining divided image sections on a color-information basis.

That is, the image generating portion 123 combines divided image sections using any one of the process of combining them on a pixel basis, that on a frequency basis, that on a bit-depth basis, and that on a color-information basis to generate a one-frame image. Alternatively, for example, when the process illustrated in FIG. 2A is used in the image dividing portion 115, the image generating portion 123 does not generate a one-frame image because an image is acquired on a one-frame basis without being divided.

The image generating portion 123 stores, in the image storage memory 124, generated one-frame images or one-frame images received from the image receiving portion 122 in an order in which the images were received by the image receiving portion 122 (transmission order). At this time, the image generating portion 123 also transmits storage information relating to the images stored in the image storage memory 124 to the display controller 125.

The image storage memory 124 temporarily stores images transmitted from the image generating portion 123.

The display controller 125 performs control such that images stored in the image storage memory 124 are displayed on the display apparatus 150 based on the transmission order of the images or capture-order information in accordance with an imaging condition input through the UI portion 140 and an operation status of the X-ray imaging apparatus 110. For example, when the imaging condition is a cine imaging mode and the operation status of the X-ray imaging apparatus 110 is during the cine imaging, the display controller 125 performs control such that images stored in the image storage memory 124 are displayed in a cine loop. When a new image is received by the image receiving portion 122 and stored in the image storage memory 124 while images are displayed on the display apparatus 150 in a cine loop, the display controller 125 displays images including the new image in a loop on the display apparatus 150 in accordance with the capture-order information. No cine-loop displaying may be performed by the display controller 125, depending on an imaging condition input through the UI portion 140.

An example method of driving the display control apparatus 120 having the configuration described above will now be described below.

First, the image generating portion 123 regenerates a one-frame image from images received by the image receiving portion 122 (divided image sections) using capture-order information received by the capture-order information receiving portion 121. At this time, when a one-frame image is received by the image receiving portion 122, the image generating portion 123 does not generate such an image.

A one-frame image generated by the image generating portion 123 or a one-frame image received by the image receiving portion 122 is stored in the image storage memory 124 from the image generating portion 123. At the same time, storage information relating to the image stored in the image storage memory 124 is transmitted from the image generating portion 123 to the display controller 125. The display controller 125 acquires an image from the image storage memory 124 based on the storage information transmitted from the image generating portion 123 in accordance with the imaging condition input through the UI portion 140 or the operation status of the X-ray imaging apparatus 110 and displays the image on the display apparatus 150.

An example method of controlling displaying performed by the display controller 125 will now be described below.

Figure 8:
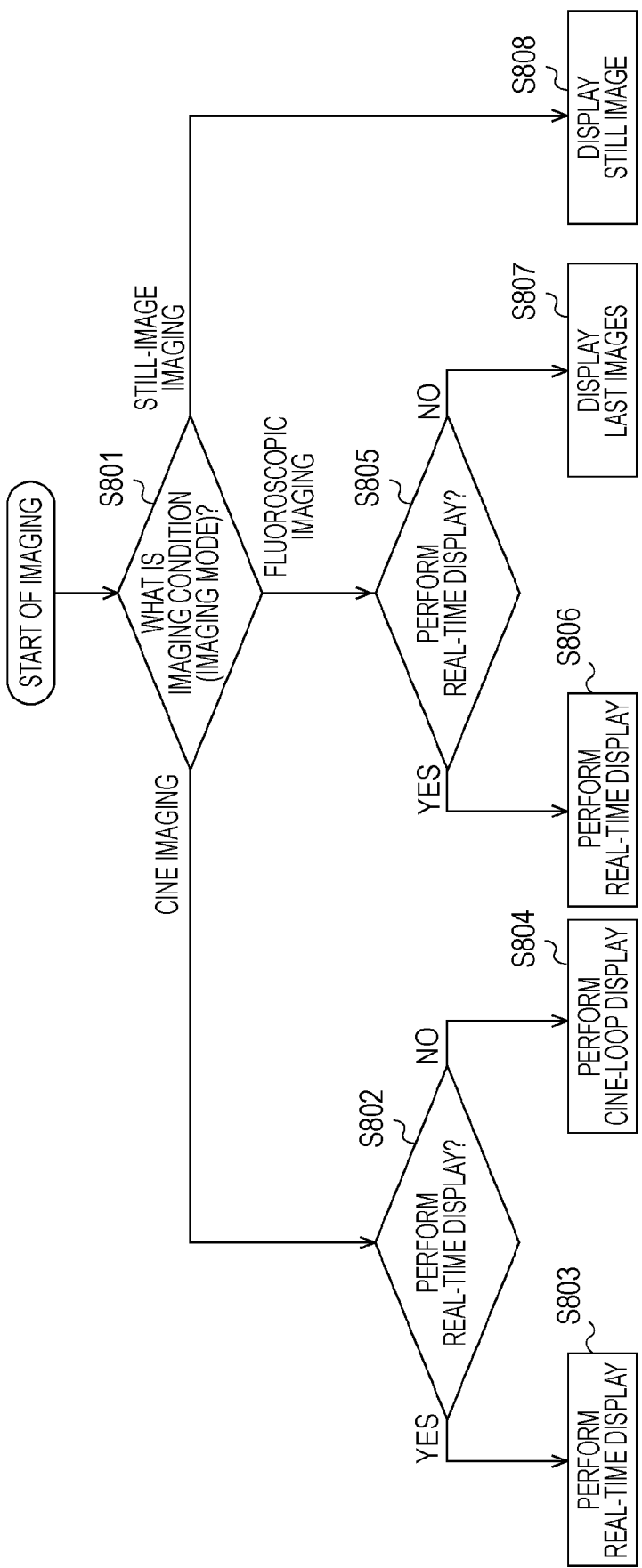
FIG. 8 is a flowchart that shows one example process of controlling displaying performed by a display controller of a display control apparatus according to an embodiment of the present invention.

FIG. 8 is a flowchart that shows one example process of controlling displaying performed by the display controller 125 of the display control apparatus 120 according to an embodiment of the present invention.

In the example illustrated in FIG. 8, as an imaging condition input through the UI portion 140, an imaging mode consisting of "cine imaging," "fluoroscopic imaging," and "still-image imaging" is used, similar to the example illustrated in FIG. 3. In this example, the chronologically dividing process illustrated in FIG. 2A (i.e., the process in which each one of images stored in the image storage memory 112 is not divided) is used, and a one-frame image is received by the image receiving portion 122.

When an imaging starts in response to an operation to the UI portion 140, in step S801, the display controller 125 determines what an imaging condition (in this embodiment, "imaging mode") input through the UI portion 140 is. If it is determined that the imaging mode is a cine imaging in step S801, flow proceeds to step S802. In step S802, the display controller 125 determines, based on information indicating the operating status of the X-ray imaging apparatus 110 input through the UI portion 140 (information that indicates whether imaging end information has been input), whether the real-time displaying is to be performed. If the imaging end information has not been input through the UI portion 140, i.e., the operating status of the X-ray imaging apparatus 110 is during the cine imaging, it is determined that real-time displaying is to be performed.

If it is determined that real-time displaying is to be performed in step S802, flow proceeds to step S803. In step S803, the display controller 125 performs real-time displaying, which is image displaying having short display delay. In this case, the display controller 125 performs control such that images stored in the image storage memory 112 are displayed on the display apparatus 150 sequentially, i.e., in a transmission order transmitted from the X-ray imaging apparatus 110.

If it is determined that real-time displaying is not to be performed in step S802, i.e., the operating status of the X-ray imaging apparatus 110 is after the cine imaging ends, flow proceeds to step S804. In step S804, the display controller 125 performs cine-loop displaying.

If it is determined that the imaging mode is a fluoroscopic imaging in step S801, flow proceeds to step S805. In step S805, the display controller 125 determines whether the real-time displaying is to be performed, based on information indicating the operating status of the X-ray imaging apparatus 110 input through the UI portion 140 (information that indicates whether imaging end information has been input). If the imaging end information has not been input through the UI portion 140, i.e., the operating status of the X-ray imaging apparatus 110 is during the fluoroscopic imaging, it is determined that real-time displaying is to be performed.

If it is determined that real-time displaying is to be performed in step S805, flow proceeds to step S806. In step S806, the display controller 125 performs real-time displaying, which is image displaying having short display delay, as in the case of the cine imaging.

If it is determined that real-time displaying is not to be performed in step S805, i.e., the operating status of the X-ray imaging apparatus 110 is after the fluoroscopic imaging ends, flow proceeds to step S807. In step S807, the display controller 125 causes the display status of the display apparatus 150 to be a status in which the last image is displayed (last image hold (LIH)).

If it is determined that the imaging mode is a still-image imaging in step S801, flow proceeds to step S808. In step S808, the display controller 125 performs control such that images stored in the image storage memory 112 are displayed on the display apparatus 150 as still images.

The cine-loop display process shown in step S804 of FIG. 8 will now be described in detail below.

Figure 9:
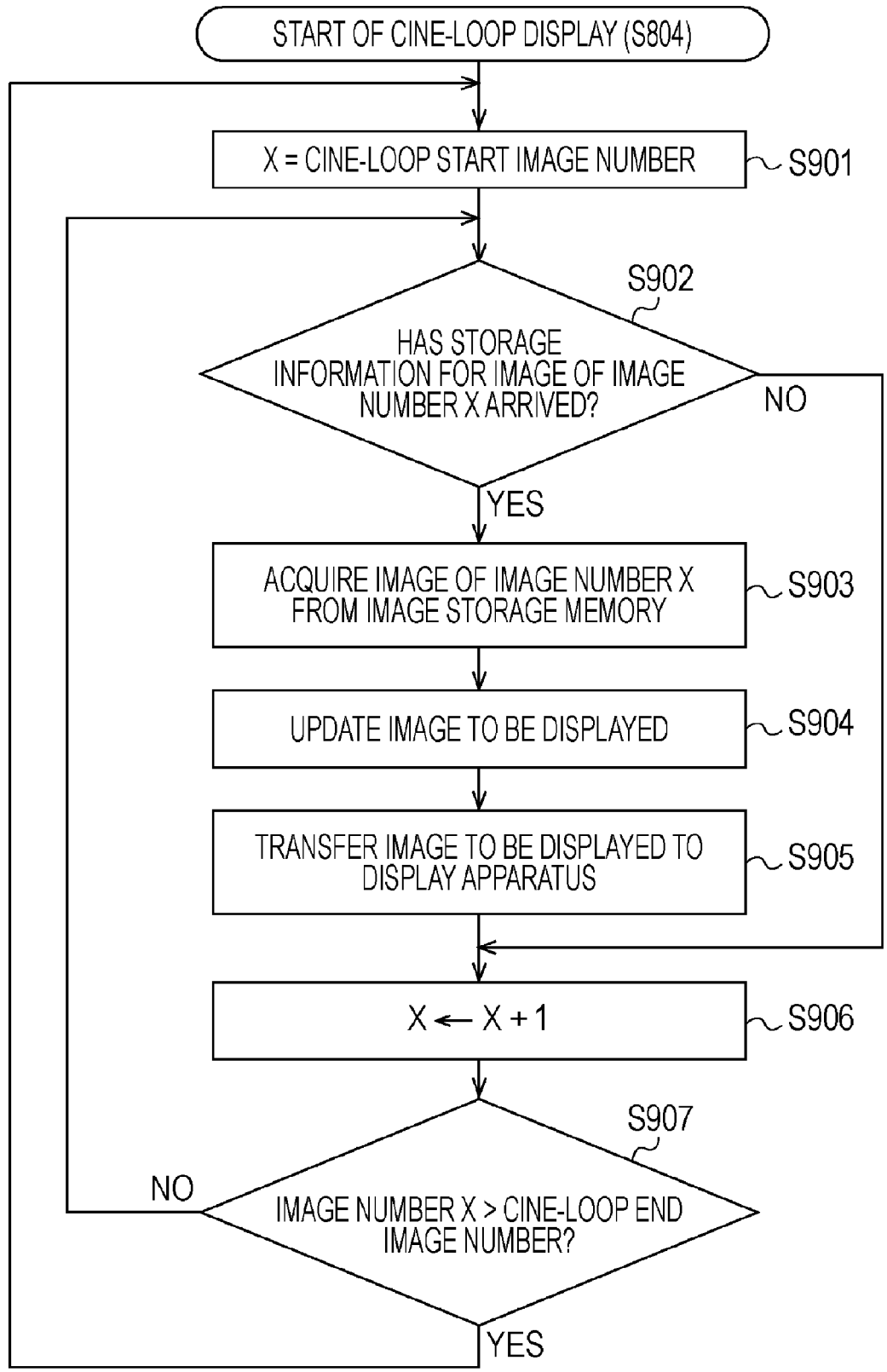
FIG. 9 is a flowchart that illustrates in detail one example process performed in cine-loop displaying illustrated in step S804 of FIG. 8.

FIG. 9 is a flowchart that illustrates in detail one example process performed in cine loop displaying shown in step S804 of FIG. 8.

When the cine-loop displaying starts, first, in step S901, the display controller 125 sets a cine-loop start image number X at which the cine loop starts, using a capture-order information. Here, for example, as the cine-loop start image number X, the number indicating a capture order in the capture-order information is assigned.

Then, in step S902, the display controller 125 determines whether storage information (which may be generation information if an image is generated) for an image of the image number X has arrived from the image generating portion 123.

If it is determined that the storage information for an image of the image number X has arrived from the image generating portion 123 in step S902, flow proceeds to step S903. In step S903, the display controller 125 acquires an image corresponding to the image number X from the image storage memory 124.

Then, in step S904, the display controller 125 updates the image of the image number as an image to be displayed. Then, in step S905, the image to be displayed updated in step S904 is transferred to the display apparatus 150, and the image to be displayed is displayed. Thereafter, flow proceeds to step S906.

If it is determined that the storage information for an image of the image number X has not arrived from the image generating portion 123 in step S902, the displayed state of the image being currently displayed on the display apparatus 150 is maintained, and flow proceeds to step S906.

Then, in step S906, the display controller 125 adds one to the cine-loop start image number X to change the cine-loop start image number X.

Then, in step S907, the display controller 125 determines whether the image number X is larger than a predetermined cine-loop end image number. If it is determined that the image number is not larger than the cine-loop end image number (i.e., is equal to or smaller), flow returns to step S902. In step S902 and the subsequent steps, an image for the cine-loop start image number X changed in step S906 is processed.

If it is determined that the image number X is larger than the cine-loop end image number in step S907, flow returns to step S901. In step S901 and the subsequent steps, an image for the first cine-loop start image number X is processed again.

Figure 10:
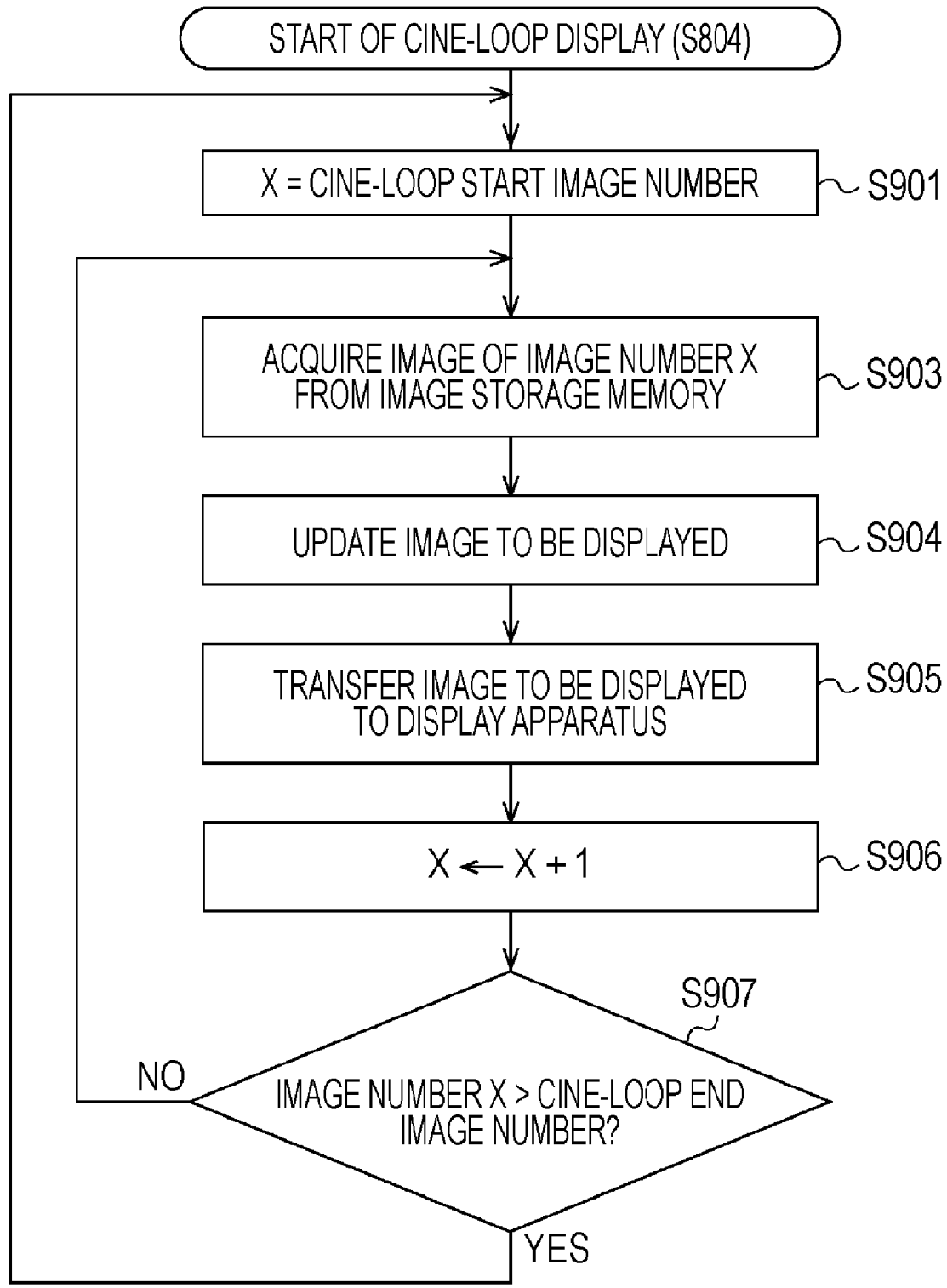
FIG. 10 is a flowchart that illustrates in detail another example process performed in cine-loop displaying illustrated in step S804 of FIG. 8.

FIG. 10 is a flowchart that illustrates in detail another example process performed in cine-loop displaying illustrated in step S804 of FIG. 8. In FIG. 10, the same step number is used in the same processing as in FIG. 9.

In the process illustrated in FIG. 10, after the processing of step S901, flow proceeds to step S903 without determination in step S902. In the process illustrated in FIG. 10, when it is assumed that storage information has arrived from the image generating portion 123 every time, the image to be displayed is updated every time.

Figure 11:
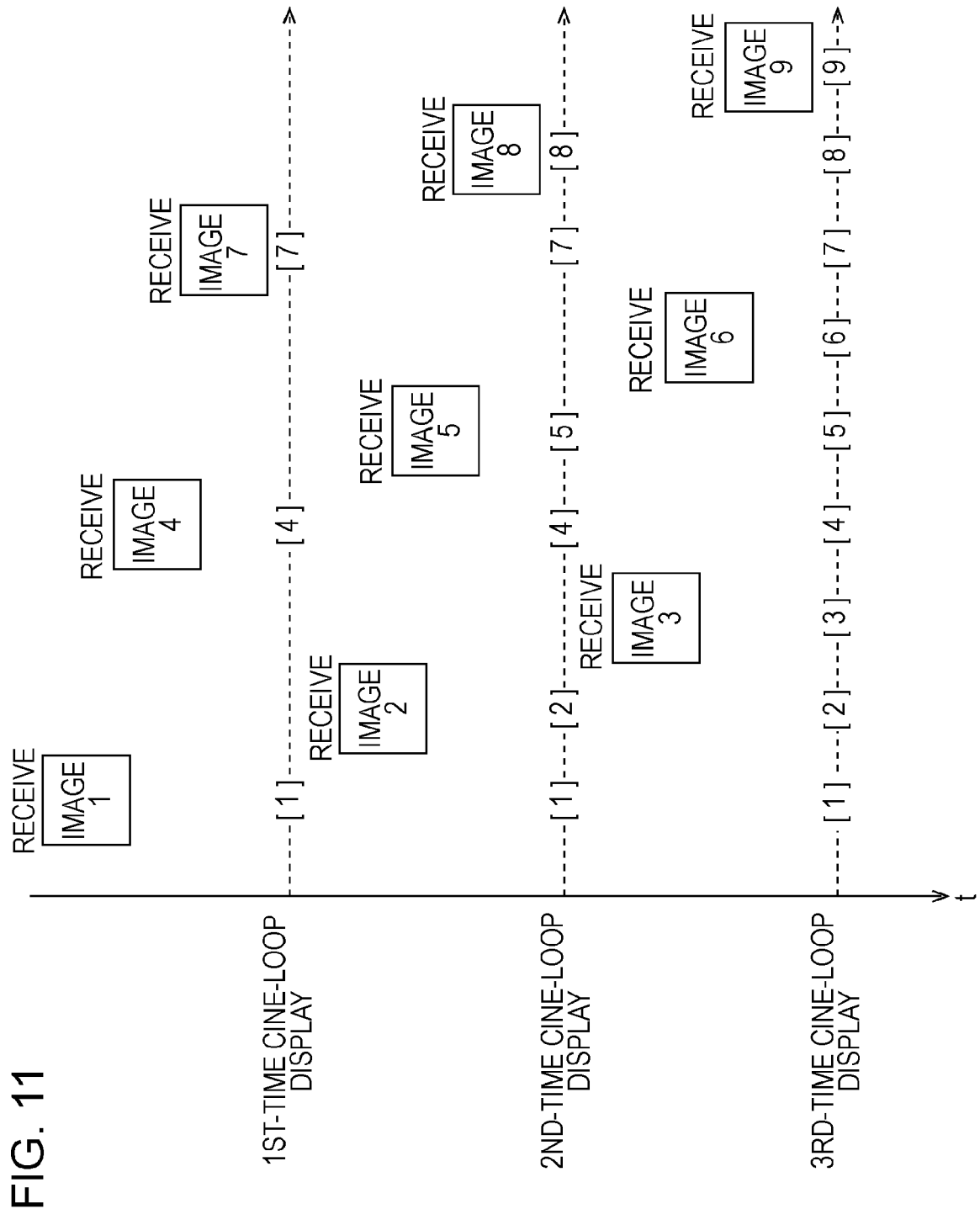
FIG. 11 is a schematic diagram that illustrates one example of cine-loop displaying performed in step S804 of FIG. 8.

FIG. 11 is a schematic diagram that illustrates one example of cine-loop displaying performed in step S804 of FIG. 8. The execution of the above-described control relating to the cine-loop displaying performed by the display controller 125 enables sequential updating of the cine-loop displaying, as illustrated in FIG. 11.

At the point of the first-time cine-loop displaying illustrated in FIG. 11, images received by the image receiving portion 122 and then stored in the image storage memory 124 are images 1, 4, and 7. In this case, the display controller 125 displays these images in a cine loop on the display apparatus 150 in order of the image 1, the image 4, and the image 7 in accordance with the capture-order information.

Then, at the point of the second-time cine-loop displaying, new images 2, 5, and 8 are received and then stored in the image storage memory 124 during the first-time cine-loop displaying. In this case, the display controller 125 displays these images in a cine loop on the display apparatus 150 in order of the image 1, the image 2, the image 4, the image 5, the image 7, and the image 8 in accordance with the capture-order information. Then, at the point of the third-time cine-loop displaying, new images 3, 6, and 9 are received and then stored in the image storage memory 124 during the second-time cine-loop displaying. In this case, the display controller 125 displays these images in a cine loop on the display apparatus 150 in order of the image 1, the image 2, the image 3, the image 4, the image 5, the image 6, the image 7, the image 8, and the image 9 in accordance with the capture-order information.

As described above, the X-ray imaging apparatus 110 transmits capture-order information indicating a capture order in which images were captured by the image capturing portion 111 to the display control apparatus 120 and also sequentially transmits images to the display control apparatus 120 in accordance with a transmission order determined by the transmission-order determining portion 113. On the other hand, the display control apparatus 120 sequentially receives the plurality of images sequentially transmitted from the X-ray imaging apparatus 110 in accordance with the determined transmission order and also receives the capture-order information indicating a capture order of each of the plurality of images. The display control apparatus 120 displays the images stored in the image storage memory 124 on the display apparatus 150 based on the transmission order of the images or the received capture-order information in accordance with an input imaging condition and an operating status of the X-ray imaging apparatus 110.

According to the aforementioned configuration, because image data is not subjected to lossy compression or sampled, a disadvantage in which degradation occurs in an image is avoidable. Because images can be displayed in real time on the display apparatus 150 in accordance with an input imaging condition or an operating status of the radiation imaging apparatus, a display delay can be suppressed. In particular, when the imaging mode relating to a cine imaging is input as the imaging condition, images can be displayed in real time, which has less display delay, during the cine imaging, whereas all images can be displayed in a cine loop after the completion of the cine imaging.

When a new image is received and then stored in the image storage memory 124 while images stored in the image storage memory 124 are displayed in a cine loop, as illustrated in FIG. 11, images including the new image are displayed in a loop in accordance with the capture-order information.

According to such a configuration, even at a stage before the stage where all images relating to cine imaging are complete (the third time in FIG. 11), images stored in the image storage memory 124 can be displayed in a cine loop. Therefore, the start time of the cine-loop displaying can be advanced, thus enabling image displaying that has less image delay.

The above-described components illustrated in FIG. 1 constituting the X-ray imaging apparatus 110 and the display control apparatus 120 of the X-ray imaging system 100 according to the present embodiment can be realized by execution of a program stored in a random-access memory (RAM) or read-only memory (ROM) performed by a central processing unit (CPU) of a computer. The steps illustrated in FIGS. 3 and 8 to 10 indicating processes performed by the X-ray imaging apparatus 110 and the display control apparatus 120 of the X-ray imaging system 100 according to the present embodiment can be realized by execution of a program stored in a RAM or ROM performed by a CPU of a computer. The program and a computer-readable storage medium are included in the present invention.

Specifically, the program can be provided to the computer through a storage medium on which the program is stored, such as a compact-disk ROM (CD-ROM), or other transmission media. Examples of the storage medium on which the program is recorded include, in addition to a CD-ROM, a flexible disk, hard disk, magnetic tape, magneto-optical disk, and non-volatile memory card. One example of the transmission media for the program can be a communication medium in a computer network (e.g., wide area network (WAN), such as local area network (LAN) and the Internet, or wireless communication network) system for propagating program information as a carrier wave to supply it. Examples of a communication medium in this case include cables, such as optical fibers, and wireless communication.

The present invention is not limited to a mode in which the functions of the X-ray imaging system 100 according to the present embodiment are realized by a computer executing a supplied program. For example, when the functions of the X-ray imaging system 100 according to the present embodiment are realized in conjunction with an operating system (OS) on which the program runs in a computer or other application software, the program is also included in the present invention. As another example, when the functions of the X-ray imaging system 100 according to the present embodiment are realized by execution of all or part of processing of the supplied program by a function expansion board or a function expansion unit, the program is also included in the present invention.

The above-described present embodiment is provided only by way of example for embodying for carrying out the present invention. The technical scope of the present invention should not be restrictively interpreted to just that embodiment. That is, the present invention can be carried out in various ways without departing from the present invention.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2007-275648 filed Oct. 23, 2007, which is hereby incorporated by reference herein in its entirety.

What is claimed is:

1. A radiation imaging apparatus for use in an environment that includes a display control apparatus, the display control apparatus for controlling displaying on a display apparatus such that the radiation imaging apparatus is able to communicate with the display control apparatus, the radiation imaging apparatus comprising:

an image capturing unit configured to capture a plurality of images;

an order-information transmitting unit configured to transmit, to the display control apparatus, capture-order information associated with each of the plurality of images and indicating a capture order in which the images were captured by the image capturing unit;

a transmission-order determining unit configured to determine priority based on an input imaging condition and information on a frequency band of a communication unit connecting the radiation imaging apparatus and the display control apparatus and determine a transmission order for transmitting each of the plurality of images to the display control apparatus in accordance with the priority and a time when each of the images was captured by the image capturing unit; and an image transmitting unit configured to sequentially transmit the plurality of images to the display control apparatus in accordance with the transmission order determined by the transmission-order determining unit.

2. The radiation imaging apparatus according to claim 1, wherein the capture-order information is determined by a time when each of the images was captured by the image capturing unit.

3. The radiation imaging apparatus according to claim 1, wherein the imaging condition is any one of an imaging mode, including cine imaging, fluoroscopic imaging, and still-image imaging, a part of a subject to be radiographed using the radiation imaging apparatus, a condition of X-rays with which a subject is to be irradiated, a frame rate for radiographing using the radiation imaging apparatus, a size of an image to be captured in the radiation imaging apparatus, a bit depth of the image to be captured in the radiation imaging apparatus, color information for the image to be captured in the radiation imaging apparatus, and a dynamic range of the image to be captured in the radiation imaging apparatus.

4. The radiation imaging apparatus according to claim 1, wherein the plurality of images transmitted from the image transmitting unit are displayed in a loop on the display apparatus in accordance with the input imaging condition and an operating status of the radiation imaging apparatus.

5. The radiation imaging apparatus according to claim 1, further comprising an image dividing unit configured to divide the plurality of images or each of the plurality of images, wherein the image transmitting unit is configured to transmit the divided images or image sections obtained by division performed by the image dividing unit to the display control apparatus based on the transmission order determined by the transmission-order determining unit.

6. The radiation imaging apparatus according to claim 5, wherein the image diving unit is configured to divide each of the plurality of images using any one of a process of dividing the image on a pixel basis, a process of dividing the image on a frequency basis, a process of dividing the image on a bit-depth basis, and a process of dividing the image on a color-information basis.

7. The radiation imaging apparatus according to claim 1, wherein the image transmitting unit comprises a plurality of image transmitting units, and any of the plurality of image transmitting units transmits an image to the display control apparatus based on the transmission order determined by the transmission-order determining unit.

8. A radiation imaging system comprising:

a display control apparatus for controlling displaying of a plurality of images captured by a radiation imaging apparatus on a display apparatus; and a radiation imaging apparatus connected to the display control apparatus so as to be able to communicate therewith;

wherein the display control apparatus includes:
  an image receiving unit configured to receive a plurality of images sequentially transmitted from the radiation imaging apparatus in accordance with a determined transmission order;
  a capture-order information receiving unit configured to receive, from the radiation imaging apparatus, capture-order information associated with each of the plurality of images and indicating a capture order in which the images were captured by the radiation imaging apparatus;
  a storage unit configured to store the images received by the image receiving unit; and
  a display control unit configured to control displaying of the images stored in the storage unit on the display apparatus based on the transmission order or the capture-order information in accordance with an input imaging condition and an operating status of the radiation imaging apparatus; and
wherein the radiation imaging apparatus includes:
  an image capturing unit configured to capture a plurality of images;
  an order-information transmitting unit configured to transmit, to the display control apparatus, capture-order information associated with each of the plurality of images and indicating a capture order in which the images were captured by the image capturing unit;
  a transmission-order determining unit configured to determine priority based on an input imaging condition and information on a frequency band of a communication unit connecting the radiation imaging apparatus and the display control apparatus and determine a transmission order for transmitting each of the plurality of images to the display control apparatus in accordance with the priority and a time when each of the images was captured by the image capturing unit; and
  an image transmitting unit configured to sequentially transmit the plurality of images to the display control apparatus in accordance with the transmission order determined by the transmission-order determining unit.

* * * * *